(12) United States Patent
Lee et al.

(10) Patent No.: US 12,290,679 B2
(45) Date of Patent: *May 6, 2025

(54) REINFORCED ELECTRODE LEADS AND METHODS FOR MANUFACTURING THE SAME

(71) Applicant: Advanced Bionics AG, Staefa (CH)

(72) Inventors: Sung Jin Lee, Valencia, CA (US); Jeryle L. Walter, Valencia, CA (US); Honggang Jiang, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/141,024

(22) Filed: Apr. 28, 2023

(65) Prior Publication Data

US 2023/0256239 A1   Aug. 17, 2023

Related U.S. Application Data

(63) Continuation of application No. 17/258,922, filed as application No. PCT/US2018/043316 on Jul. 23, 2018, now Pat. No. 11,691,003.

(51) Int. Cl.
*A61N 1/05* (2006.01)
*A61N 1/36* (2006.01)
*A61N 1/375* (2006.01)

(52) U.S. Cl.
CPC ....... *A61N 1/0541* (2013.01); *A61N 1/36038* (2017.08); *A61N 1/375* (2013.01)

(58) Field of Classification Search
CPC ... A61N 1/0541; A61N 1/36038; A61N 1/375
See application file for complete search history.

(56) References Cited

U.S. PATENT DOCUMENTS 3,760,812 A  *  9/1973  Timm ............... A61N 1/05
                                                607/116
5,231,996 A     8/1993  Bardy et al.
                (Continued)

FOREIGN PATENT DOCUMENTS

| EP | 2564892 | 3/2013 |
| WO | 2014116912 | 7/2014 |
| WO | 2015030739 | 3/2015 |

OTHER PUBLICATIONS

"International Search Report and Written Opinion received in International Application No. PCT/US2018/043316 received Apr. 1, 2019."

(Continued)

*Primary Examiner* — Eric D. Bertram
(74) *Attorney, Agent, or Firm* — ALG Intellectual Property, LLC

(57) ABSTRACT

An exemplary electrode lead includes a flexible body formed of a flexible insulating material and that comprises a fantail region that connects to a cochlear implant configured to be implanted within a recipient and that extends to a ground electrode located toward a proximal end of the electrode lead, an electrode contact disposed on a side of the flexible body, a coiled electrode wire provided within the flexible body so as to extend along a length of the flexible body and electrically connect the electrode contact to a signal source, and a coiled reinforcing element provided within the flexible body so as to extend together with the coiled electrode wire along the length of the flexible body. The coiled reinforcing element may only be provided within a proximal portion of the electrode lead. Corresponding methods of manufacturing an electrode lead are also described.

19 Claims, 11 Drawing Sheets

(56) References Cited

U.S. PATENT DOCUMENTS

| | | | |
|---|---|---|---|
| 5,330,521 A * | 7/1994 | Cohen | A61N 1/05 607/122 |
| 5,454,795 A * | 10/1995 | Samson | C08L 79/08 604/526 |
| 5,674,272 A | 10/1997 | Bush et al. | |
| 5,951,539 A * | 9/1999 | Nita | A61M 25/005 604/524 |
| 6,152,912 A * | 11/2000 | Jansen | A61M 25/0053 604/524 |
| 7,519,432 B2 | 4/2009 | Bolea et al. | |
| 7,831,311 B2 * | 11/2010 | Cross, Jr. | A61N 1/056 607/116 |
| 8,321,028 B1 | 11/2012 | Thenuwara et al. | |
| 8,366,699 B2 * | 2/2013 | Jimenez | A61M 25/0053 604/524 |
| 8,515,556 B2 | 8/2013 | Ries et al. | |
| 8,781,599 B2 * | 7/2014 | Henshaw | A61N 1/0488 607/137 |
| 8,825,171 B1 | 9/2014 | Thenuwara et al. | |
| 9,044,589 B2 * | 6/2015 | Raje | A61N 1/0541 |
| 9,839,778 B2 | 12/2017 | Zimmerling et al. | |
| 11,691,003 B2 * | 7/2023 | Lee | A61N 1/375 607/57 |
| 2002/0123738 A1 * | 9/2002 | Jansen | A61M 25/0053 604/526 |
| 2004/0002727 A1 * | 1/2004 | Hwang | A61M 25/005 606/194 |
| 2006/0089697 A1 * | 4/2006 | Cross, Jr. | A61N 1/056 607/122 |
| 2013/0110215 A1 * | 5/2013 | Fan | A61N 1/362 977/925 |
| 2013/0238074 A1 | 9/2013 | Zimmerling | |
| 2014/0094892 A1 * | 4/2014 | Thenuwara | A61N 1/0541 607/137 |
| 2016/0030735 A1 | 2/2016 | Ouchouche | |
| 2016/0144164 A1 | 5/2016 | Sedighiani | |
| 2016/0339234 A1 | 11/2016 | Zimmerling et al. | |
| 2019/0329027 A1 * | 10/2019 | Hudak | A61N 1/0541 |

OTHER PUBLICATIONS

Sanchez, D., "Design Considerations for Using Reinforced Silicone Tube", Medical Product Outsourcing Aug. 10, 2017. www.mpo-mag.com/contents/view_online-exclusives/2017-08-10/design-considerations-for-usingreinforced-silicone-tube/.

* cited by examiner

REINFORCED ELECTRODE LEADS AND METHODS FOR MANUFACTURING THE SAME

RELATED APPLICATIONS

This application is a continuation application of U.S. patent application Ser. No. 17/258,922, filed Jan. 8, 2021 and issued as U.S. Pat. No. 11,691,003, which is a U.S. National Stage Application under 35 U.S.C. § 371 of International Application No. PCT/US2018/043316, filed on Jul. 23, 2018, each of which is hereby incorporated by reference in its entirety.

BACKGROUND INFORMATION

Cochlear implant systems are used to provide, restore, and/or improve the sense of hearing to recipients with severe or profound hearing loss. A key component of a cochlear implant system is an electrode lead that is inserted into a cochlea of the recipient in a delicate surgical procedure referred to herein as an "insertion procedure." A typical electrode lead includes conductive wires that are provided within an electrode lead body formed of an insulating biocompatible material.

To facilitate insertion of the electrode lead during the insertion procedure, the electrode lead is typically formed to be flexible so that the electrode lead can conform to the spiral shape of the human cochlea when implanted in the recipient. Such flexibility is typically achieved by using soft silicone tubing for the electrode lead body and very thin conductive wires (e.g., 20-25 µm in diameter). However, these conductive wires are fragile, and the soft silicone tubing used for the electrode lead body is, in certain circumstances, not strong enough by itself to sufficiently protect the conductive wires. As a result, the conductive wires may be broken or damaged during manufacturing, packaging, handling, the insertion procedure, and/or impact (e.g., from a traumatic injury to the head of the recipient).

U.S. Pat. No. 3,760,812 ("Timm") discloses implantable spiral wound stimulation electrodes. For example, Timm discloses a stimulation electrode that includes conductor wires and spacer strands that are wrapped helically around a flexible cylindrical insulative core such that the spacer strands are provided between adjacent winds of the conductor wires. In Timm, the conductor wires and alternating spacer strands are maintained in a desired relationship by insulative strands that are helically wound in the opposite direction from the conductor wires and the spacer strands, that have substantially the same spacing as the conductor wires and the spacer strands, and that are interwoven with the conductor wires and the spacer strands.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
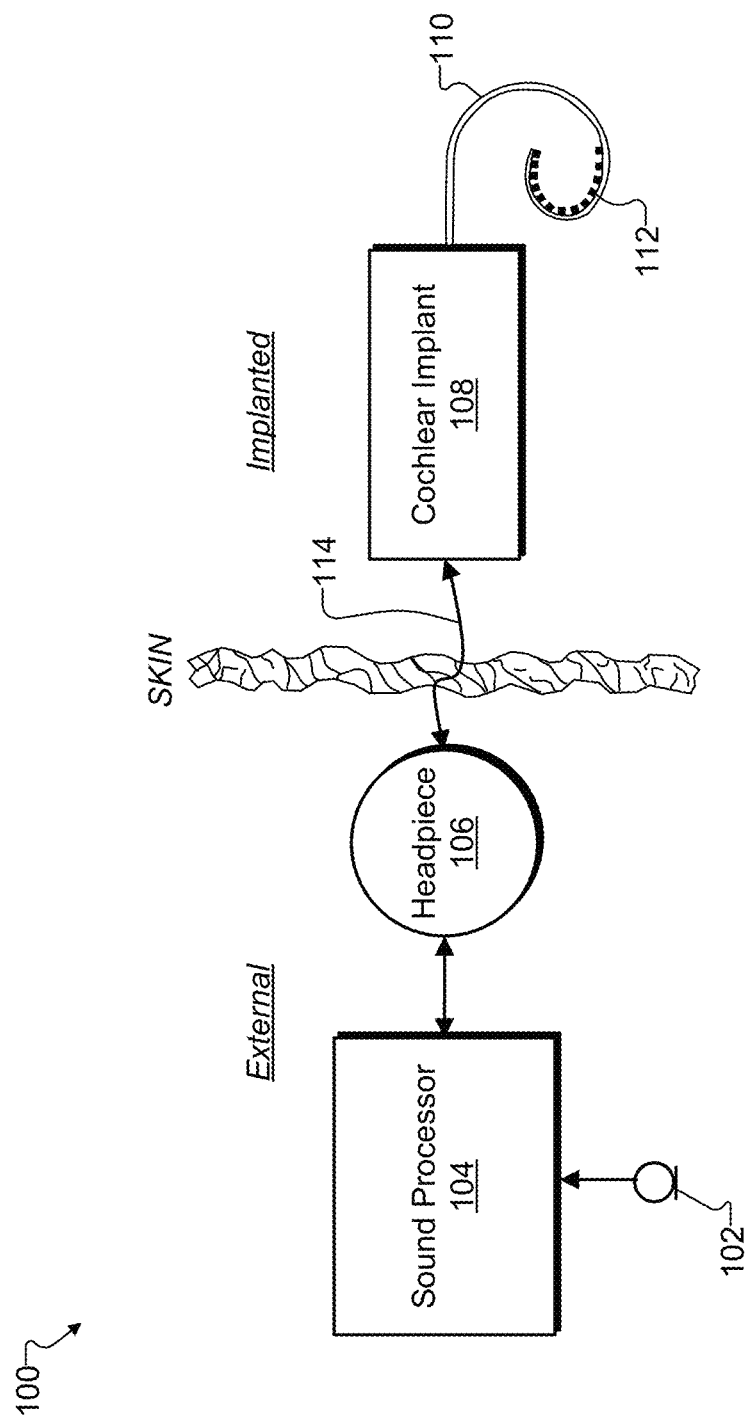
FIG. 1 illustrates an exemplary cochlear implant system according to principles described herein.

Reinforced electrode leads and methods for manufacturing the same are described herein. As will be described in more detail below, an exemplary electrode lead described herein includes a flexible body formed of a flexible insulating material and an electrode contact disposed on a side of the flexible body. The electrode lead further includes a coiled electrode wire provided within the flexible body so as to extend along a length of the flexible body and electrically connect the electrode contact to a signal source. The electrode lead further includes a coiled reinforcing element provided within the flexible body so as to extend together with the coiled electrode wire along the length of the flexible body. A winding direction of the coiled electrode wire is opposite a winding direction of the coiled reinforcing element. A winding pitch of the coiled electrode wire is smaller than a winding pitch of the coiled reinforcing element.

For example, the coiled electrode wire may be wound in a clockwise direction and the coiled reinforcing element may be wound in a counterclockwise direction, or vice versa. Such a configuration helps protect the coiled electrode wire from damage in circumstances where torsion is provided in a direction opposite to the winding direction of the coiled electrode wire. Typically, when torsion is provided to a coiled electrode wire is such a direction, the coiled electrode wire has a propensity to kink, which could damage or break the coiled electrode wire. However, when the coiled reinforcing element is wound in a winding direction opposite the winding direction of the coiled electrode wire, the coiled reinforcing element provides a resistive force that causes the electrode lead to resist being twisted in the direction opposite to the winding direction of the coiled electrode wire. As such, coiled reinforcing elements such as those described herein help prevent damage that may be caused due to kinking of the coiled electrode wire.

Configuring the winding pitch of the coiled electrode wire to be smaller than the winding pitch of the coiled reinforcing element also helps prevent damage to the coiled electrode wire. For example, such a configuration helps prevent damage to the coiled electrode wire when the electrode lead is in tension (i.e., when stretched) because the relatively larger winding pitch of the coiled reinforcing element causes the coiled reinforcing element to tighten earlier than the coiled electrode wire. As a result, the coiled reinforcing element is able to absorb tensile stress that would otherwise be applied to the coiled electrode wire, thus protecting the coiled electrode wire from being damaged. In contrast, if a coiled reinforcing element has the same or smaller winding pitch as a coiled electrode wire, the coiled electrode wire may tighten earlier than the coiled reinforcing element when the electrode lead is stretched. As a result, the coiled electrode wire may be subjected to all or most of the tensile stress instead of the coiled reinforcing element, which could cause damage to the coiled electrode wire if the coiled electrode wire is stretched to a breaking point. Accordingly, by making a winding pitch of coiled reinforcing elements such as those described herein larger than a winding pitch of a coiled electrode wire, the coiled reinforcing elements are configured to protect the coiled electrode wire from being damaged.

The electrode leads described herein may provide various benefits to cochlear implant recipients, as well as to surgeons and others involved with insertion procedures. For example, because the electrode leads described herein include one or more reinforcing elements, the electrode leads are less susceptible to being damaged during packaging, transport, and/or handling, for example, by support staff prior to the insertion procedure. In addition, the electrode leads described herein are less susceptible to being damaged or broken during an insertion procedure compared with conventional electrode leads. Moreover, electrode leads such as those described herein have increased mechanical strength at a fantail region as compared with conventional electrode leads, which results in a decreased likelihood that the electrode lead will be damaged due to, for example, an impact to the recipient's head where the electrode lead is connected to an implanted cochlear implant. Accordingly, cochlear implant systems that use electrode leads such as those described herein are more robust and potentially have a longer operational life than cochlear implant systems that use conventional electrode leads.

Various embodiments will now be described in more detail with reference to the figures. The disclosed apparatus and methods may provide one or more of the benefits mentioned above and/or various additional and/or alternative benefits that will be made apparent herein.

FIG. 1 illustrates an exemplary cochlear implant system 100. As shown, cochlear implant system 100 may include a microphone 102, a sound processor 104, a headpiece 106 having a coil disposed therein, a cochlear implant 108, and an electrode lead 110. Electrode lead 110 may include an array of electrodes 112 disposed on a distal portion of electrode lead 110 and that are configured to be inserted into the cochlea to stimulate the cochlea after the distal portion of electrode lead 110 is inserted into the cochlea. It will be understood that one or more other electrodes (e.g., including a ground electrode, not explicitly shown in FIG. 1) may also be disposed on other parts of electrode lead 110 (e.g., on a proximal portion of electrode lead 110) to, for example, provide a current return path for stimulation current generated by electrodes 112 and to remain external to the cochlea after electrode lead 110 is inserted into the cochlea. Various embodiments of electrode lead 110 will be described herein. Additional or alternative components may be included within cochlear implant system 100 as may serve a particular implementation. For example, a pre-curved electrode lead and/or a straight electrode lead may alternatively be used in connection with cochlear implant 108.

As shown, cochlear implant system 100 may include various components configured to be located external to a recipient including, but not limited to, microphone 102, sound processor 104, and headpiece 106. Cochlear implant system 100 may further include various components configured to be implanted within the recipient including, but not limited to, cochlear implant 108 and electrode lead 110.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, input by way of a device like the Clinical Programming Interface ("CPI") device from Advanced Bionics, etc.) to one or more stimulation sites associated with an auditory pathway (e.g., the auditory nerve) of the recipient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may be housed within any suitable housing (e.g., a behind-the-ear ("BTE") unit, a body worn device, headpiece 106, and/or any other sound processing unit as may serve a particular implementation).

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108 (e.g., a wireless link between a coil disposed within headpiece 106 and a coil physically coupled to cochlear implant 108). It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the recipient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a recipient and configured to apply stimulation to one or more stimulation sites located along an auditory pathway of a recipient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites (e.g., one or more intracochlear regions) within the recipient via electrodes 112 disposed along electrode lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
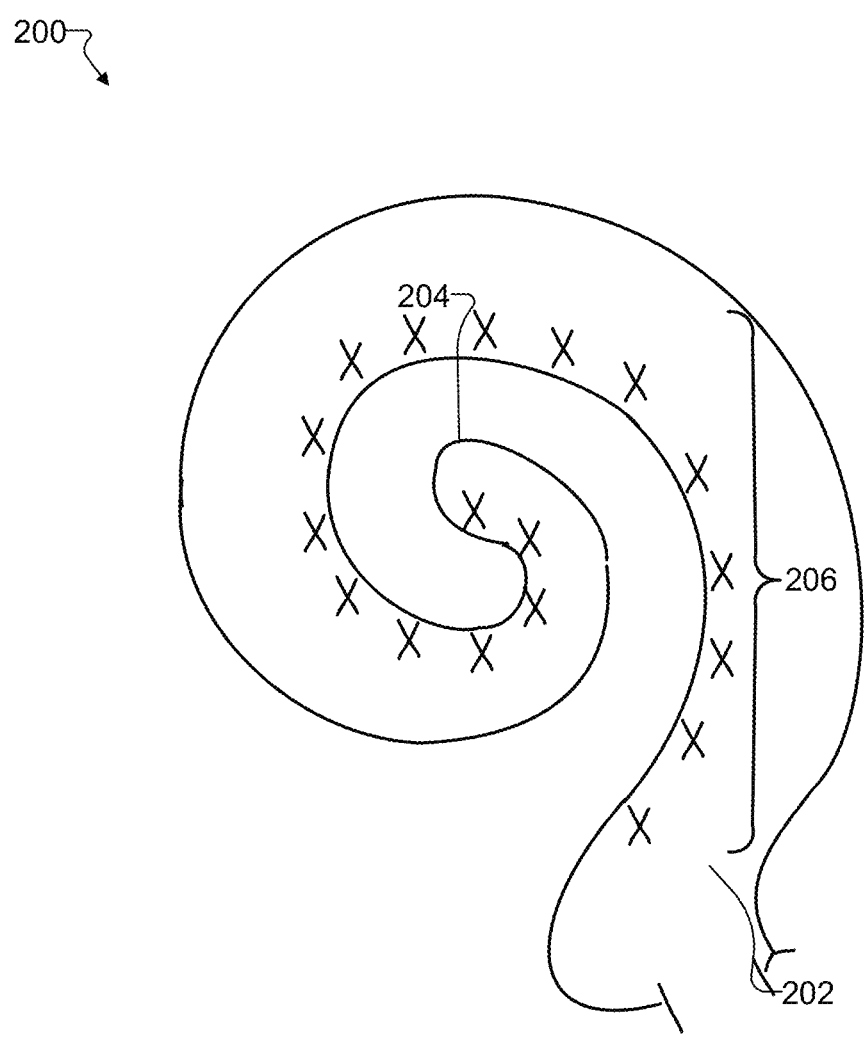
FIG. 2 illustrates a schematic structure of the human cochlea according to principles described herein.

FIG. 2 illustrates a schematic structure of the human cochlea 200 into which electrode lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the recipient perceiving relatively low frequencies and electrical stimulation applied by way of electrodes disposed within the basal region (i.e., "basal electrodes") may result in the recipient perceiving relatively high frequencies. The delineation between the apical and basal electrodes on a particular electrode lead may vary depending on the insertion depth of the electrode lead, the anatomy of the recipient's cochlea, and/or any other factor as may serve a particular implementation.

Figure 3:
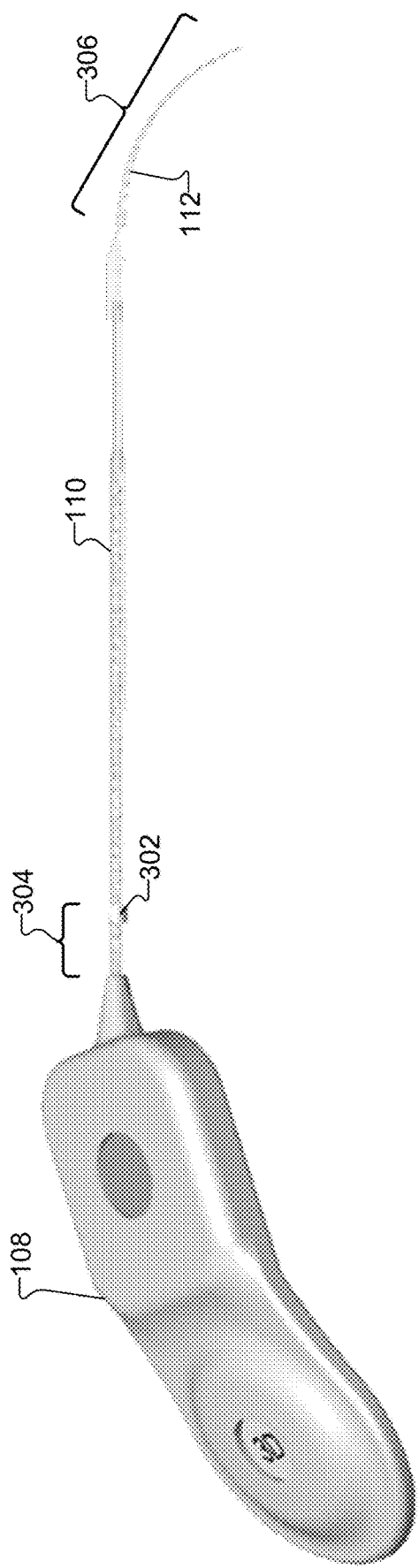
FIG. 3 illustrates exemplary components of the cochlear implant system that are configured to be implanted in a recipient according to principles described herein.

FIG. 3 illustrates an exemplary depiction of components of cochlear implant system 100 that are configured to be implanted in a recipient. For example, FIG. 3 shows cochlear implant 108 communicatively coupled to electrode lead 110 with electrodes 112 disposed along electrode lead 110. FIG. 3 also shows a ground electrode 302 disposed on a proximal portion of lead 110 and that is configured to provide a return path for current delivered to electrodes 112. As shown in FIG. 3, electrode lead 110 includes a fantail region 304 provided towards a proximal end of electrode lead 110, where electrode lead 110 connects to cochlear implant 108. Electrode lead 110 also includes a distal region 306 that is provided towards a distal end of electrode lead 110 and that is configured to be inserted in the cochlea of a recipient. In some instances, fantail region 304 may generally be considered as a region of electrode lead 110 that is provided between ground electrode 302 and cochlear implant 108. Distal region 306 may generally be considered as a region of electrode lead 110 that is provided between a most proximal electrode included in electrodes 112 and a distal end of electrode lead 110.

Cochlear implant 108 is configured to provide electrical stimulation to the one or more stimulation sites by way of a plurality of electrode wires (not shown in FIG. 3) that are provided within electrode lead 110 and that electrically connect electrodes 112 to one or more signal sources within cochlear implant 108. The electrode wires may be formed of any suitable conductive material. In certain examples, the electrode wires may be formed of coiled 20-25 µm metal wires that are fragile and that may easily be broken or get damaged during packaging, handling, surgery, etc. The electrode wires are particularly susceptible to being broken or damaged in fantail region 304. This is in part because fantail region 304 is located on an outer surface of the skull when implanted within a recipient whereas the rest of electrode lead 110 is located under the skull. This causes the mechanical strength of the electrode wires to be significantly changed in fantail region 304 (i.e., a stress gradient of the electrode wires in fantail region 304 is relatively higher than in other regions). Damage to the electrode wires included in electrode lead 110 may result in either sub-optimal function or loss of function of cochlear implant system 100.

As will be described herein, to protect electrode wires within electrode lead 110 from breaking or otherwise being damaged, electrode lead 110 may include one or more coiled reinforcing elements configured to mechanically strengthen electrode lead 110. Coiled reinforcing elements such as such as those described herein may be configured in any manner as may suit a particular implementation. For example, a coiled reinforcing element may include a coiled wire, fiber, strand, ribbon, group of wires, group of fibers, group of strands, group of ribbons, etc., or any suitable combination thereof. A coiled reinforcing element may be made of any suitable material as may serve a particular implementation. For example, a coiled reinforcing element may be formed of a biocompatible polymer wire, fiber, strand, or ribbon. Examples of biocompatible polymers that may be used to form a coiled reinforcing element include polyethylene, ultra-high-modulus polyethylene (UHMPE), polyether ether ketone (PEEK), polyamide (nylon), etc. Various exemplary coiled reinforcing elements that may be used to reinforce electrode lead 110 will now be described with reference to FIGS. 4-9.

Figure 4:
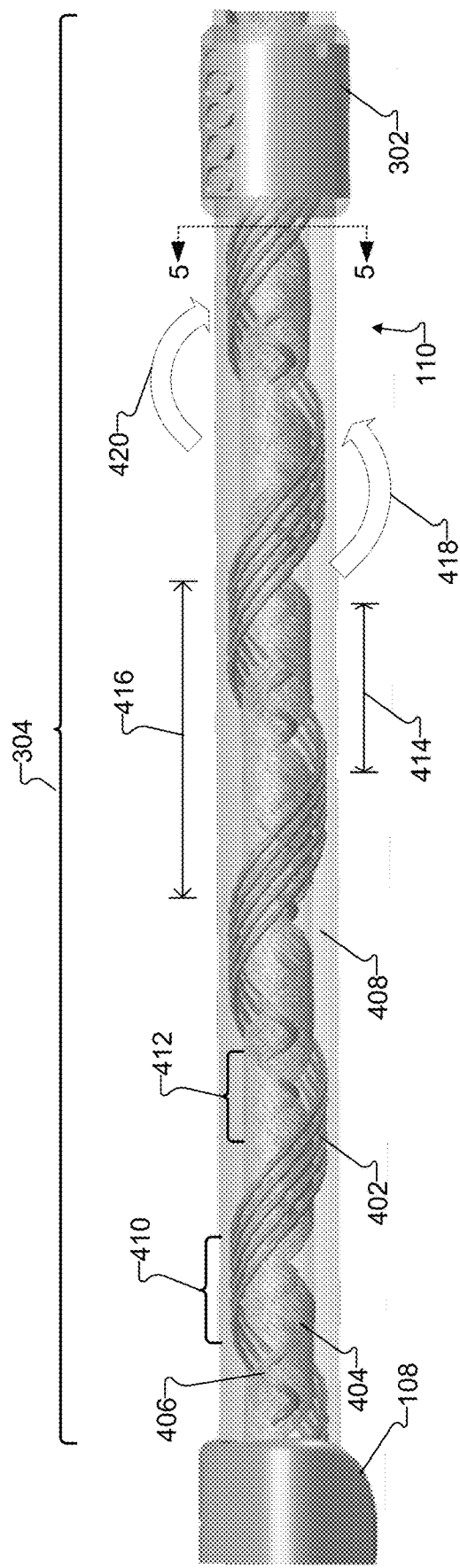
FIG. 4 illustrates an enlarged fantail region of an exemplary electrode lead having a coiled reinforcing element according to principles described herein.

FIG. 4 shows an enlarged view of fantail region 304 of electrode lead 110 that includes a plurality of coiled reinforcing elements 402 ("coiled reinforcing elements 402"), a plurality of coiled electrode wires 404 ("coiled electrode wires 404"), and a coiled grounding wire 406 that connects to ground electrode 302. Coiled reinforcing elements 402, coiled electrode wires 404, and coiled grounding wire 406 are provided within a flexible body 408.

Flexible body 408 may be formed of any suitable biocompatible insulating material that is sufficiently flexible to bend during the insertion procedure. In certain examples, flexible body 408 is formed of silicone. However, any other suitable insulating material may be used in certain implementations. Although only a portion of flexible body 408 is shown in FIG. 4, it is understood that flexible body 408 may be provided along the entire length of electrode lead 110.

Coiled reinforcing elements 402 may include any number of reinforcing elements as may serve a particular implementation. For example, in the example of FIG. 4, coiled reinforcing elements 402 include five reinforced reinforcing elements. As shown, coiled reinforcing elements 402 may be bundled together and helically wound along a length of flexible body 408. As such, coiled reinforcing elements 402 form a plurality of helically formed groups of windings extending within flexible body 408 along the length of flexible body 408. In FIG. 4, winding group 410 represents one group of windings included in the plurality of helically formed groups of windings of coiled reinforcing elements 402. Each winding group included in the plurality of helically formed groups of windings of coiled reinforcing elements 402 may be spaced apart from a successive winding group by approximately the same amount along the length of flexible body 408.

Coiled electrode wires 404 may include any number of electrode wires (e.g., sixteen) as may serve a particular implementation. As shown, coiled electrode wires 404 are also bundled together and helically wound along the length of flexible body 408. As such, coiled electrical wires 404 form a plurality of helically formed groups of windings extending within flexible body 408 along the length of flexible body 408. Winding group 412 represents one group of windings included in the plurality of helically formed groups of windings of coiled electrode wires 404. Each winding group included in the plurality of helically formed groups of windings of coiled electrode wires 404 may be spaced apart from a successive winding group by approximately the same amount along the length of flexible body 408.

As shown in FIG. 4, a winding pitch 414 of coiled electrode wires 404 is smaller than a winding pitch 416 of coiled reinforcing elements 402. With such a configuration, when electrode lead 110 is in tension, the relatively larger winding pitch of coiled reinforcing elements 402 causes coiled reinforcing elements 402 to tighten earlier than coiled electrode wires 404, thus protecting coiled electrode wires 404 from being damaged.

As used herein, a "winding pitch" refers to a distance between successive windings included a plurality of helically formed windings formed out of the same reinforcing element or wire. For example, a coiled electrode wire may include a plurality of helically formed windings extending along a length of a flexible body. The plurality of helically formed windings of the coiled electrode wire may include a first winding, a second winding, and a third winding arranged successively in that order along the length of the flexible body. In such an example, the winding pitch of the coiled electrode wire may be a distance between successive windings (e.g., the first winding and the second winding) included in the plurality of helically formed windings.

Similarly, a winding pitch of a coiled reinforcing element may correspond to a distance between successive windings (e.g., a first winding and a second winding) included in a plurality of helically formed windings of the coiled reinforcing element. In certain examples, successive windings of a coiled reinforcing element may be directly adjacent to one another. For example, the first winding may be directly adjacent to the second winding and the second winding may be directly adjacent to a third winding along the length of the flexible body. Alternatively, in certain examples described herein, one or more windings of an additional coiled reinforcing element may be provided between, for example, the first winding and the second winding of the coiled reinforcing element.

In the example shown in FIG. 4, winding pitch 414 corresponds to a distance between successive windings groups of coiled electrode wires 404 that are directly adjacent to one another (e.g., winding group 412 and the successive winding group of coiled electrode wires 404 directly to the right of winding 412). Likewise, winding pitch 416 corresponds to a distance between successive windings groups of coiled reinforcing elements 402 that are directly adjacent to one another (e.g., winding group 410 and the successive winding group included in coiled reinforcing elements 402 directly to the right of winding 410).

A winding pitch of a coiled electrode wire may be any suitable amount smaller than a winding pitch of coiled a coiled reinforcing element. In the example shown in FIG. 4, winding pitch 416 of coiled reinforcing elements 402 is approximately two times the length of winding pitch 414 of coiled electrode wires 404.

A winding pitch may be measured in any suitable manner. In certain examples, when the electrode lead is viewed in a direction perpendicular to the length of the electrode lead, the winding pitch may be measured from one side of a winding to the same side of a successive winding. For example, the winding pitch may be measured from a distal side of one winding to a distal side of a successive winding of the same coiled reinforcing element. Alternatively, the winding pitch may be measured from a center of a winding to a center of a successive winding when viewed in the direction perpendicular to the length of the electrode lead. For example, winding pitch 416 is a distance measured from a distalmost portion of a winding included in one group of windings to a distalmost portion of a winding included in a successive (i.e., immediately adjacent) group of windings included in the plurality of helically formed groups of windings of coiled reinforcing elements 402.

As shown in FIG. 4, a winding direction (indicated by arrow 418) of coiled reinforcing elements 402 is opposite a winding direction (indicated by arrow 420) of coiled electrode wires 404. For example, coiled reinforcing elements 402 are wound in a counterclockwise direction whereas coiled electrode wires 404 are wound in a clockwise direction. As explained above, such a configuration is desirable because torsion in a direction opposite to the winding direction of coiled electrode wires 404 may cause coiled electrode wires 404 to get damaged or broken due to coiled electrode wires 404 being kinked. However, when coiled reinforcing elements 402 are wound in a winding direction opposite the winding direction of coiled electrode wires 404, coiled reinforcing elements 402 provide a resistive force that prevents such kinking of coiled electrode wires 404.

Figure 5:
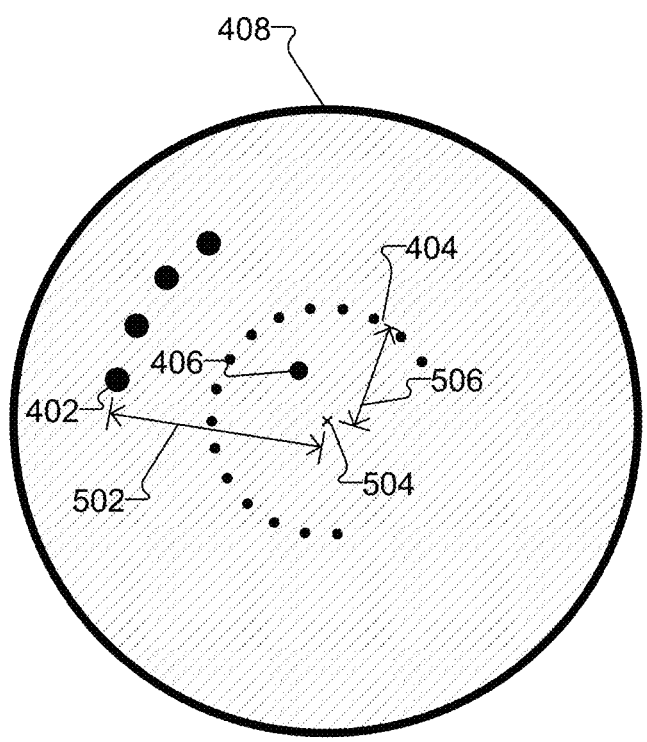
FIG. 5 illustrates an exemplary cross section of the electrode lead shown in FIG. 4 that is taken along line 5 in FIG. 4 according to principles described herein.

In certain examples, a coiled reinforcing element may be provided at a different distance in a radial direction from a longitudinally-extending center axis of electrode lead 110 than a coiled electrode wire. To illustrate, FIG. 5 depicts an enlarged cross-sectional view of electrode lead 110 taken along line 5-5 in FIG. 4. As shown in FIG. 5, coiled reinforcing elements 402 are provided at a first distance 502 in a radial direction (i.e., at a first radius) from longitudinally-extending center axis 504 of electrode lead 110 whereas coiled electrode wires 404 are provided at a second distance 506 in the radial direction (i.e., at a second radius) from longitudinally-extending center axis 504 of electrode lead 110. In the example shown in FIG. 5, the first distance 502 is greater than the second distance 506. However, in certain other implementations, first distance 502 may be smaller than second distance 506 such that coiled reinforcing elements 402 are provided closer to longitudinally-extending center axis 504 than coiled electrode wires 404.

Coiled reinforcing elements such as those described herein may have any suitable cross-sectional shape as may suit a particular implementation. In the example shown in FIG. 5, coiled reinforcing elements 402 have a circular-shaped cross-section. However, in certain implementations a coiled reinforcing element may have, for example, a square, oval, or rectangular cross-sectional shape.

In addition, coiled reinforcing elements such as those described herein may have any suitable size (e.g., diameter) as may suit a particular implementation. In certain examples, the diameter of a coiled reinforcing element may be less than 20-100 μm to avoid significant increase in the size of flexible body 410 and to maintain sufficient flexibility of electrode lead 110.

In the example shown in FIG. 5, coiled reinforcing elements 402, coiled electrode wires 404, and coiled grounding wire 406 are embedded within flexible body 408 such that coiled reinforcing elements 402 are separated from coiled electrode wire 404 in the radial direction by a portion of flexible body 408.

In certain alternative examples, a coiled reinforcing element may be wrapped around a coiled electrode wire as opposed to being spaced apart from coiled reinforcing elements in the radial direction. When a coiled reinforcing element is wrapped around a coiled electrode wire, the coiled reinforcing element may be in direct contact with at least some portions of the coiled electrode wire in the radial direction. In addition, when a coiled reinforcing element is wrapped around a coiled electrode wire, each portion of the coiled reinforcing element may be provided farther from longitudinally-extending center axis 504 of electrode lead 110 than the coiled electrode wire.

In certain examples, a coiled reinforcing element and a coiled electrode wire may be provided within a lumen of flexible body 408. In such examples, the lumen may be pre-formed in flexible body 408. The coiled reinforcing element and the coiled electrode wire may be wound with respect to one another, such as described herein, and inserted within the lumen of flexible body 408 during manufacture of electrode lead 110. To illustrate, FIG. 6 shows an exemplary fantail region 304 of electrode lead 110 in which coiled electrode wires 404 and a plurality of coiled reinforcing elements 602 ("coiled reinforcing elements 602") are provided within a lumen 604 of flexible body 408.

Figure 6:
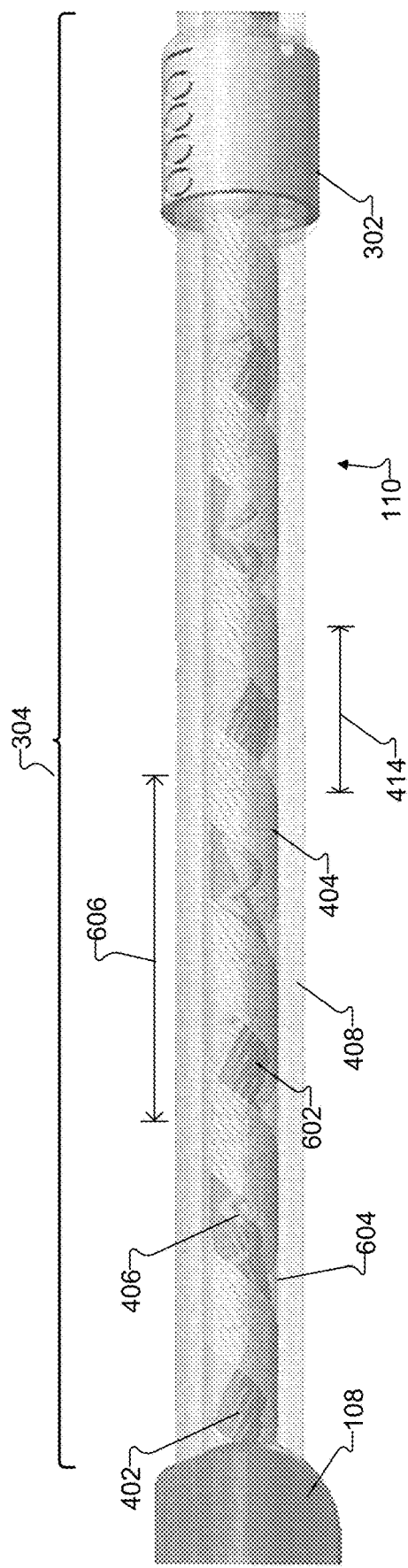
FIGS. 6-9 illustrate enlarged fantail regions of additional exemplary electrode leads according to principles described herein.

In the example shown in FIG. 6, coiled reinforcing elements 602 are provided closer to longitudinally extending center axis 504 of electrode lead 110 than coiled electrode wires 404 such that each portion of coiled electrode wires 404 is provided farther from longitudinally-extending center axis 504 of electrode lead 110 than coiled reinforcing elements 602. Although FIG. 6 shows coiled electrode wires 404 being provided around coiled reinforcing wires within lumen 604, it is understood that in certain alternative examples a coiled reinforcing element may be provided around a coiled electrode wire and the combination of the coiled reinforcing element and the coiled electrode wire may then be inserted within lumen 604.

In the example shown in FIG. 6, each coiled reinforcing element included in coiled reinforcing elements 602 is bundled together so as to form a plurality of helically formed groups of windings extending along the length of flexible body 408. However, it is understood that in certain implementations a single coiled reinforcing element (e.g., a single coiled ribbon, strand, fiber, etc.) may be provided closer to longitudinally-extending center axis 504 of electrode lead 110 than coiled electrode wires 404.

In the example shown in FIG. 6, a winding pitch 606 of coiled reinforcing elements 602 corresponds to a distance between successive groups of winding groups included in the plurality of helically formed groups of windings of coiled reinforcing elements 602. Similar to the example shown in FIG. 4, winding pitch 414 of coiled electrode wires 404 is smaller than winding pitch 606 of coiled reinforcing elements 602. In addition, a winding direction of coiled electrode wires 404 is opposite a winding direction of coiled reinforcing elements 602. Although the example shown in FIG. 6 has been described as including lumen 604, it is understood that, in certain examples, the configuration shown in FIG. 6 could be formed without including lumen 604. For example, coiled reinforcing elements 602, coiled electrode wires 404, and coiled grounding wire 406 may be placed in an electrode lead mold and a flexible insulating material may be provided in any suitable manner within the electrode lead mold such that the flexible insulating material surrounds coiled reinforcing elements 602, coiled electrode wires 404, and coiled grounding wire 406.

Figure 7:
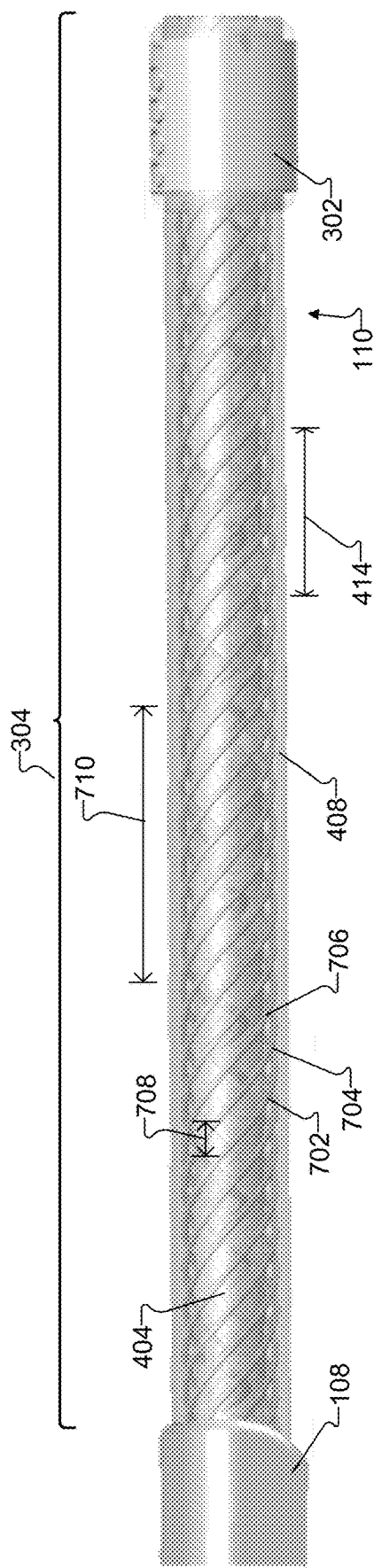

FIG. 7 shows an alternative implementation in which a plurality of coiled reinforcing elements (e.g., a first coiled reinforcing element 702, a second coiled reinforcing element 704, a third coiled reinforcing element 706, etc.) are implemented as separate strands that are wound along the length of flexible body 408 without crossing over one another. As shown, the coiled reinforcing elements are spaced apart from each other by approximately the same distance 708 along flexible body 408.

First coiled reinforcing element 702, second coiled reinforcing element 704, and third coiled reinforcing element 706 are separate strands from one another that are wound along the length of flexible body 408 without crossing over one another (i.e., the separate strands are not braided together). Because of this, in the example shown in FIG. 7, there are a plurality of windings of other coiled reinforcing elements (e.g., second coiled reinforcing element 704, third coiled reinforcing element 706, etc.) that are provided between successive windings of first coiled reinforcing element 702. Similar to the example shown in FIG. 4, a winding pitch 710 of each coiled reinforcing element (e.g., first coiled reinforcing element 702) is larger than winding pitch 414 of coiled electrode wires 404. In addition, as shown in FIG. 7, each of the coiled reinforcing elements has a winding direction that is opposite a winding direction of coiled electrode wires 404.

Figure 8:
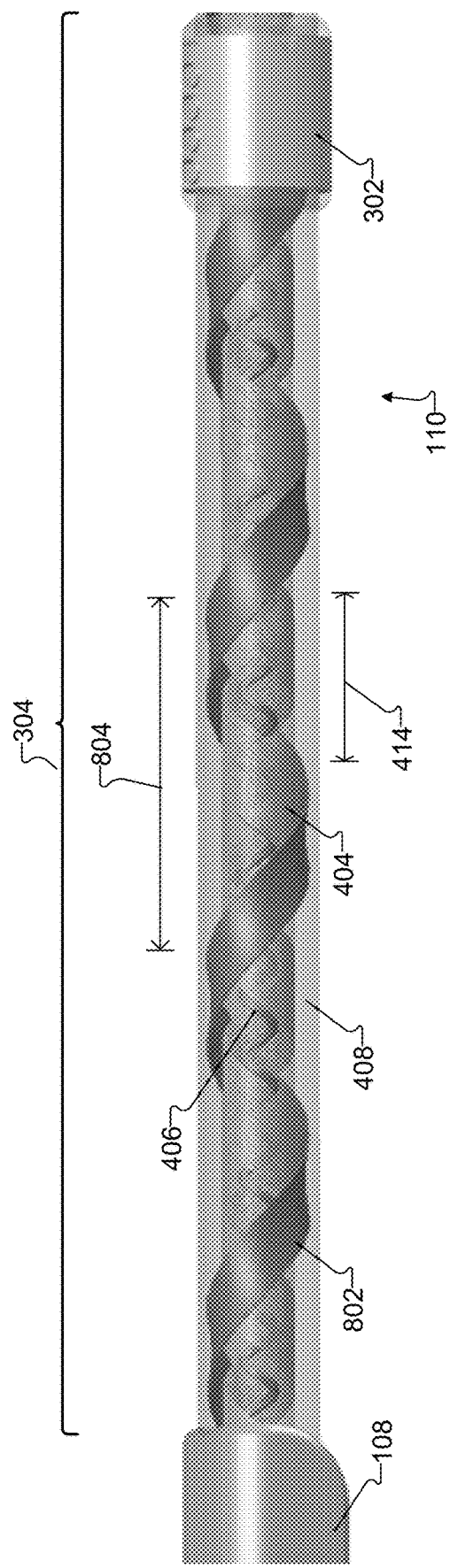

In certain examples, a coiled reinforcing element may include only a single strand that includes a plurality of helically formed windings extending within flexible body 408. To illustrate, FIG. 8 shows an exemplary fantail region 304 of electrode lead 110 in which a single ribbon-shaped coiled reinforcing element 802 ("coiled reinforcing element 802") is provided. Although coiled reinforcing element 802 is in the shape of a ribbon, it is understood that any other suitable shape for a single strand reinforcing element may be used in certain implementations. Similar to the example shown in FIG. 4, a winding pitch 804 of coiled reinforcing element 802 is larger than winding pitch 414 of coiled electrode wires 404. In addition, as shown in FIG. 8, coiled reinforcing element 802 has a winding direction that is opposite a winding direction of coiled electrode wires 404.

Figure 9:
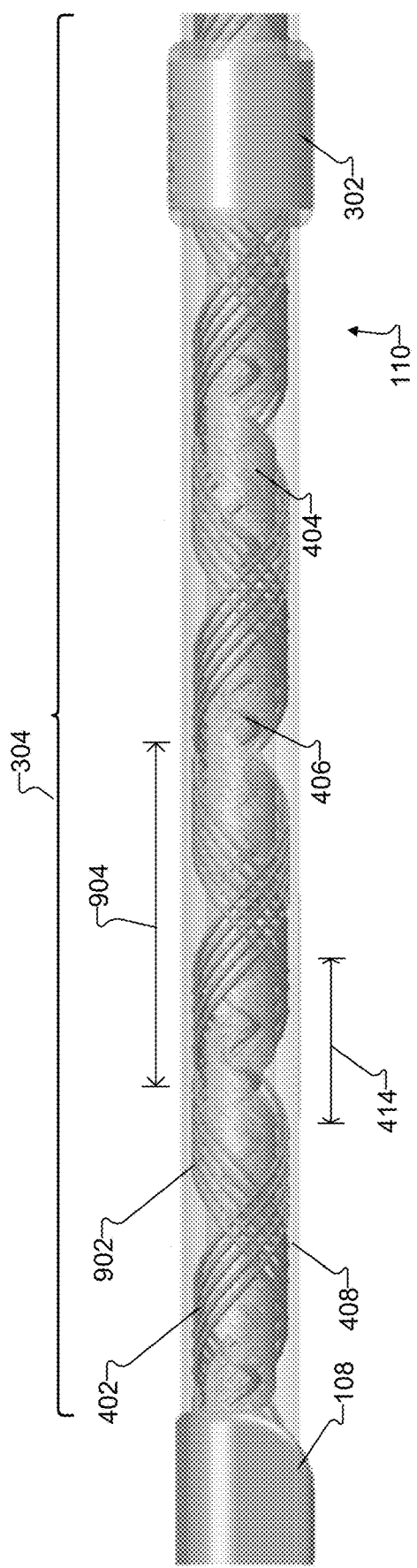

In certain examples, electrode lead 110 may include an additional coiled reinforcing element that has a winding direction opposite to the winding direction of coiled reinforcing element 402. To illustrate, FIG. 9 shows an exemplary fantail region 304 of electrode lead 110 in which a plurality of additional coiled reinforcing elements 902 ("coiled reinforcing elements 902") are provided together with coiled reinforcing elements 402. In the example shown in FIG. 9, coiled reinforcing elements 902 are bundled together so as to form a plurality of groups of helically formed windings. As shown in FIG. 9, coiled reinforcing elements 902 are wound in a clockwise direction whereas coiled reinforcing elements 402 are wound in a counterclockwise direction. Accordingly, the winding direction of coiled reinforcing elements 902 is opposite the winding direction of coiled reinforcing elements 402.

When such an additional coiled reinforcing element is provided within flexible body 408, the additional coiled reinforcing element may also have a winding pitch that is larger than coiled electrode wires 404. For example, FIG. 9 shows that coiled reinforcing elements 902 have a winding pitch 904 that is approximately two times larger than winding pitch 414 of coiled electrode wires 404.

Although only fantail region 304 is illustrated in FIGS. 4-9, it is understood that one or more coiled reinforcing elements, such as those described herein, may extend along any portion of electrode lead 110 as may suit a particular implementation. For example, coiled reinforcing elements 402 shown in FIG. 4 may only be provided in a portion of electrode lead 110 (e.g., only in fantail region 304). Alternatively, coiled reinforcing elements 402 may extend substantially along the entire length of electrode lead 110 (e.g., so as to include fantail region 304, distal region 306, and any portion of electrode lead 110 therebetween). Additionally or alternatively, coiled reinforcing elements 402 may extend proximally into cochlear implant 108 together with the electrode wires (e.g., inside the portion of cochlear implant 108 illustrated in FIG. 4).

Although the various examples of electrode leads described herein are provided in the context of a cochlear implant system, it is understood that principles such as those described herein could be applied to any type of electrode lead where it may be desirable to increase the mechanical strength of the electrode lead and prevent damage to an electrode wire included in the electrode lead.

Figure 10:
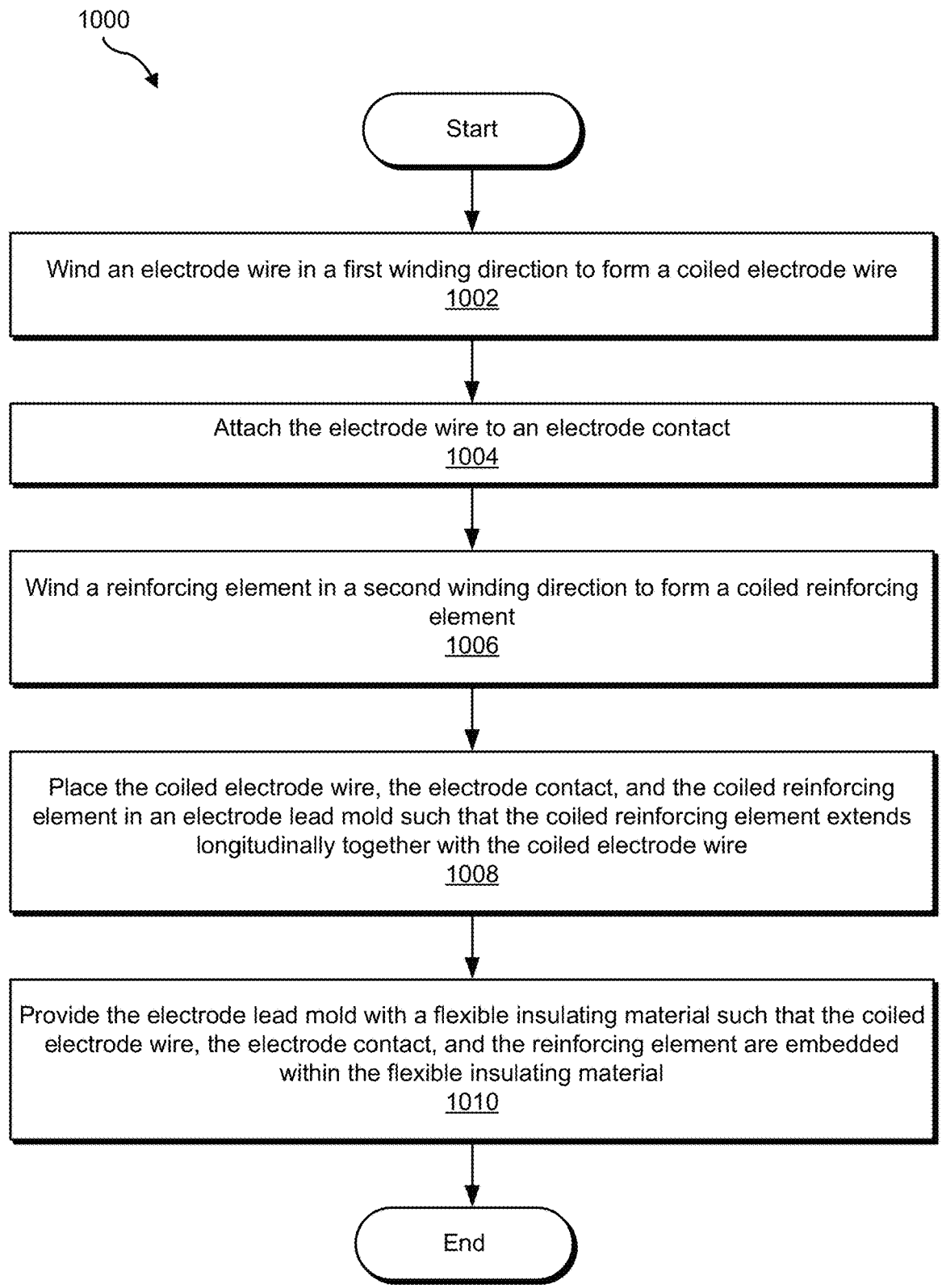
FIGS. 10 and 11 show exemplary methods for manufacturing a reinforced electrode lead having a coiled reinforcing element according to principles described herein.

FIG. 10 illustrates a method 1000 for manufacturing a reinforced electrode lead (e.g., electrode lead 110). While FIG. 10 illustrates exemplary operations according to one embodiment, other embodiments may omit, add to, reorder, and/or modify any of the operations shown in FIG. 10.

In operation 1002, an electrode wire is wound in a first winding direction to form a coiled electrode wire. The electrode wire may be wound in any suitable manner. For example, the electrode wire may be wound around a mandrel to form a plurality of helically formed windings. Operation 1002 may be performed in any of the ways described herein.

In operation 1004, the electrode wire is attached to an electrode contact (e.g., one of electrodes 112). The electrode wire may be attached in any suitable manner. For example, an electrode wire may be welded to each electrode contact included in a plurality of electrode contacts. Operation 1004 may be performed in any of the ways described herein.

In operation 1006, a reinforcing element is wound in a second winding direction to form a coiled reinforcing element. The second winding direction is opposite the first winding direction. The reinforcing element may be wound in the second winding direction in any suitable manner. In certain examples, the reinforcing element may be wound in the second winding direction around a mandrel to form a plurality of helically formed windings. Alternatively, the winding of the reinforcing element in the second winding direction may include winding the reinforcing element around the coiled electrode wire. In addition, the winding of the reinforcing element may be performed such that a winding pitch of the coiled reinforcing element is larger than a winding pitch of the coiled electrode wire. Operation 1006 may be performed in any of the ways described herein.

In certain examples, operation 1006 may be performed prior to operation 1002 such that the reinforcing element is wound in the second winding direction prior to the electrode wire being wound in the first winding direction. In such examples, the electrode wire may be wound around the reinforcing element instead of being wound around a mandrel.

In operation 1008, the coiled electrode wire, the electrode contact, and the coiled reinforcing element are placed in an electrode lead mold such that the coiled reinforcing element extends longitudinally together with the coiled electrode wire. Operation 1008 may be performed in any of the ways described herein.

In operation 1010, the electrode lead mold is provided with a flexible insulating material (e.g., silicone) such that the coiled electrode wire, the electrode contact, and the reinforcing element are embedded within the flexible insulating material. The electrode lead mold may be provided with the flexible insulating material in any suitable manner. In certain examples, the flexible insulating material may be injected into the electrode lead mold such that such that the flexible body is formed when the flexible insulating material solidifies. In such examples, the flexible insulating material embeds the coiled reinforcing element, the coiled electrode wire, and the electrode contact. Alternatively, the flexible insulating material may be compression molded in the electrode lead mold (e.g., by providing the flexible insulating material in a first half of the electrode lead mold and then pressing a second half of the electrode lead mold onto the flexible insulating material provided in the first half of the electrode lead mold). Operation 1010 may be performed in any of the ways described herein.

Figure 11:
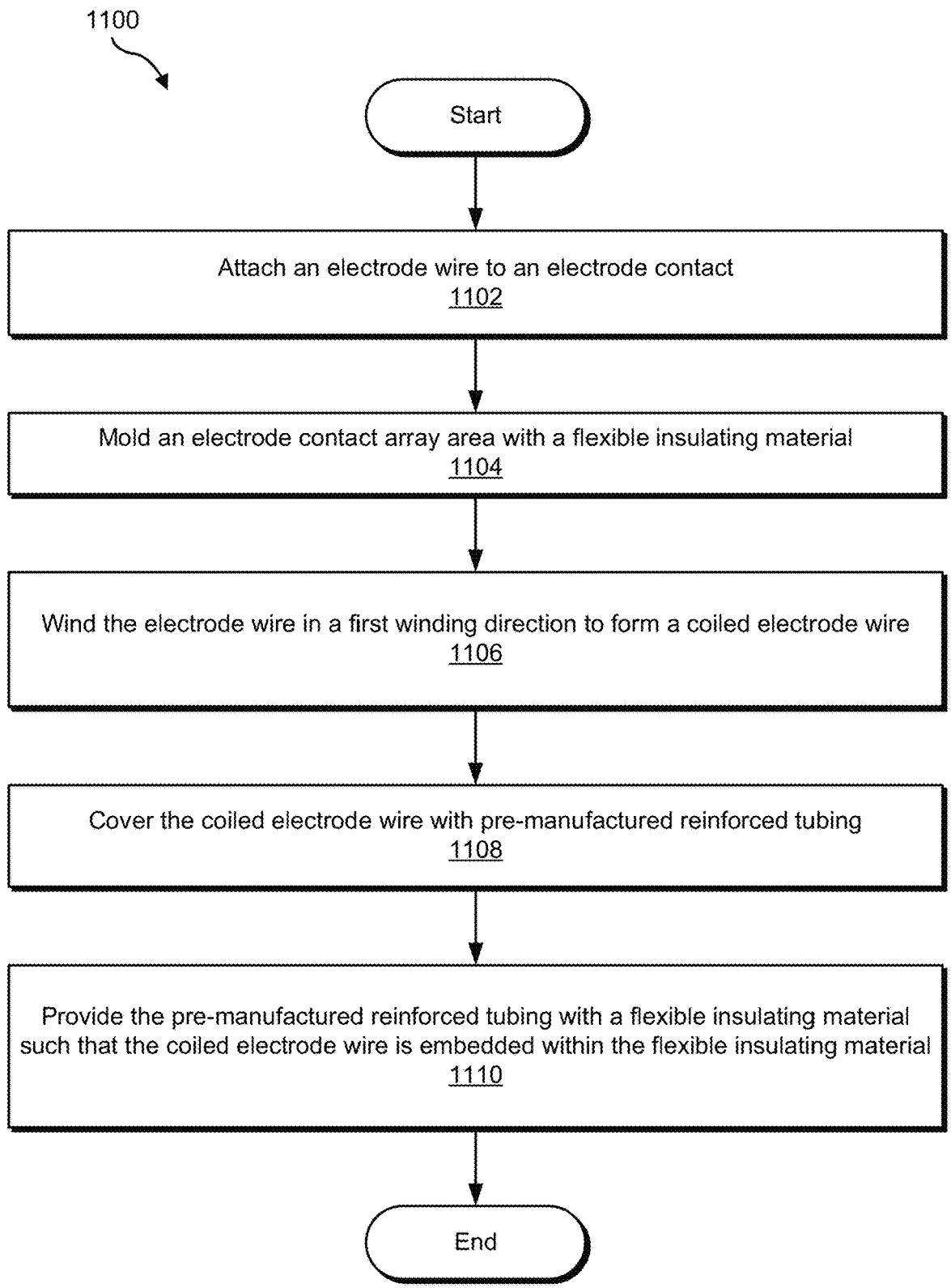

In certain alternative examples, a method for manufacturing a reinforced electrode lead (e.g., electrode lead 110) may include utilizing pre-manufactured reinforced tubing (e.g., silicone tubing) that is obtained from a tubing manufacturer and that already has a coiled reinforcing element embedded therein. FIG. 11 illustrates a method 1100 for manufacturing a reinforced electrode lead (e.g., electrode lead 110) according to such alternative examples. While FIG. 11 illustrates exemplary operations according to one embodiment, other embodiments may omit, add to, reorder, and/or modify any of the operations shown in FIG. 11.

In operation 1102, an electrode wire is attached to an electrode contact (e.g., one of electrodes 112). The electrode wire may be attached in any suitable manner. For example, an electrode wire may be welded to each electrode contact included in a plurality of electrode contacts. Operation 1102 may be performed in any of the ways described herein.

In operation 1104, an electrode contact array area is molded with a flexible insulating material. The electrode contact array area may be molded in any suitable manner. For example, silicone may be provided in any suitable manner with respect to a plurality of electrode contacts to form the electrode contact array area. Operation 1104 may be performed in any of the ways described herein.

In operation 1106, the electrode wire is wound in a first winding direction to form a coiled electrode wire. The electrode wire may be wound in any suitable manner. For example, the electrode wire may be wound around a mandrel to form a plurality of helically formed windings. Operation 1106 may be performed in any of the ways described herein.

In operation 1108, the coiled electrode wire is covered with pre-manufactured reinforced tubing (e.g., silicone tubing). The pre-manufactured reinforced tubing may be provided so as to cover the coiled electrode wire in any suitable manner. For example, the coiled electrode wire may be inserted into a lumen of the pre-manufactured reinforced tubing. The pre-manufactured reinforced tubing includes a reinforcing element that is embedded within a wall of the of the pre-manufactured reinforced tubing and that is wound in a second winding direction is opposite the first winding direction. In addition, the reinforcing element in the pre-manufactured reinforced tubing has a winding pitch that is larger than a winding pitch of the coiled electrode wire. Operation 1108 may be performed in any of the ways described herein.

In operation 1110, the pre-manufactured reinforced tubing is provided with a flexible insulating material (e.g., silicone) such that the coiled electrode wire is embedded within the flexible insulating material. The flexible insulating material may be provided in any suitable manner. For example, the flexible insulating material may be injected within a lumen of the pre-manufactured reinforced tubing such that the flexible insulating material fills the lumen and embeds the coiled electrode wire when the flexible insulating material solidifies. Operation 1110 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An electrode lead adapted for insertion into a human body, comprising:
a flexible body formed of a flexible insulating material and that comprises a fantail region that connects to a cochlear implant configured to be implanted within a recipient and that extends to a ground electrode located toward a proximal end of the electrode lead;
an electrode contact disposed on a side of the flexible body;
a coiled electrode wire provided within the flexible body so as to extend along a length of the flexible body and electrically connect the electrode contact to a signal source; and
a coiled reinforcing element provided within the flexible body so as to extend together with the coiled electrode wire along the length of the flexible body,
wherein:
the electrode contact is provided within a distal portion of the electrode lead; and
the coiled reinforcing element:
is only provided within a proximal portion of the electrode lead that does not include the distal portion; and
is only provided in the fantail region of the flexible body that is in the proximal portion of the electrode lead.

2. The electrode lead of claim 1, wherein:
a winding direction of the coiled electrode wire is opposite a winding direction of the coiled reinforcing element; and
a winding pitch of the coiled electrode wire is smaller than a winding pitch of the coiled reinforcing element.

3. The electrode lead of claim 2, wherein:
the coiled electrode wire includes a plurality of helically formed windings extending along the length of the flexible body;
the winding pitch of the coiled electrode wire corresponds to a distance between successive windings included in the plurality of helically formed windings;
the coiled reinforcing element includes a plurality of additional helically formed windings extending along the length of the flexible body; and
the winding pitch of the coiled reinforcing element corresponds to a distance between successive windings included in the plurality of additional helically formed windings.

4. The electrode lead of claim 2, wherein:
the coiled electrode wire includes a plurality of coiled electrode wires;
each coiled electrode wire included in the plurality of coiled electrode wires is bundled together so as to form a plurality of helically formed groups of windings extending along the length of the flexible body; and
the winding pitch of the coiled electrode wire corresponds to a distance between successive groups of windings included in the plurality of helically formed groups of windings.

5. The electrode lead of claim 2, wherein:
the coiled reinforcing element includes a plurality of coiled reinforcing elements;
each coiled reinforcing element included in the plurality of coiled reinforcing elements is bundled together so as to form a plurality of helically formed groups of windings extending along the length of the flexible body; and
the winding pitch of the coiled reinforcing element corresponds to a distance between successive groups of windings included in the plurality of helically formed groups of windings.

6. The electrode lead of claim 2, wherein:
the coiled reinforcing element includes a plurality of coiled reinforcing elements;
each coiled reinforcing element included in the plurality of coiled reinforcing elements includes a plurality of helically formed windings extending along the length of the flexible body;
successive helically formed windings included in the plurality of helically formed windings are spaced apart from each other by a same distance along the length of the flexible body; and
the winding pitch of the coiled reinforcing element corresponds to a distance between helically formed windings included in the plurality of helically formed windings of a particular coiled reinforcing element included in the plurality of coiled reinforcing elements.

7. The electrode lead of claim 2, wherein:
the coiled reinforcing element comprises a single ribbon that includes a plurality of helically formed windings extending along the length of the flexible body; and
the winding pitch of the coiled reinforcing element corresponds to a distance between successive windings included in the plurality of helically formed windings of the single ribbon.

8. The electrode lead of claim 1, wherein:
the coiled reinforcing element is provided at a first distance in a radial direction from a longitudinally-extending center axis of the electrode lead;
the coiled electrode wire is provided at a second distance in the radial direction from the longitudinally-extending center axis of the electrode lead; and
the first distance is greater than the second distance.

9. The electrode lead of claim 1, wherein:
the coiled reinforcing element is provided at a first distance in a radial direction from a longitudinally-extending center axis of the electrode lead;
the coiled electrode wire is provided at a second distance in the radial direction from the longitudinally-extending center axis of the electrode lead; and
the first distance is smaller than the second distance.

10. The electrode lead of claim 1, further comprising an additional coiled reinforcing element that has a winding direction opposite to a winding direction of the coiled reinforcing element.

11. The electrode lead of claim 1, wherein the coiled reinforcing element is embedded within the flexible body.

12. The electrode lead of claim 1, wherein the coiled reinforcing element is wound around the coiled electrode wire.

13. The electrode lead of claim 1, wherein:
the flexible body includes a lumen that extends along the length of the flexible body; and
the coiled electrode wire and the coiled reinforcing element are provided within the lumen of the flexible body.

14. The electrode lead of claim 1, wherein the coiled reinforcing element is a polymer strand.

15. An electrode lead adapted for insertion into a human cochlea, comprising:
a flexible body formed of a flexible insulating material and that comprises a fantail region that connects to a cochlear implant configured to be implanted within a recipient and that extends to a ground electrode located toward a proximal end of the electrode lead;
a plurality of electrode contacts disposed on a side of the flexible body;
a plurality of coiled electrode wires provided within the flexible body and that electrically connect the plurality of electrode contacts to a signal source, each coiled electrode wire included in the plurality of coiled electrode wires being bundled together so as to form a plurality of helically formed groups of windings extending along a length of the flexible body; and
a coiled reinforcing element provided within the flexible body and including a plurality of helically formed windings extending along the length of the flexible body together with the plurality of helically formed groups of windings of the plurality of coiled electrode wires,
wherein:
the plurality of electrode contacts is provided within a distal portion of the electrode lead; and
the coiled reinforcing element:
is only provided within a proximal portion of the electrode lead that does not include the distal portion; and
is only provided in the fantail region of the flexible body that is in the proximal portion of the electrode lead.

16. The electrode lead of claim 15, wherein:
a winding pitch of the plurality of coiled electrode wires corresponds to a distance between successive groups of windings included in the plurality of helically formed groups of windings; and
a winding pitch of the coiled reinforcing element corresponds to a distance between successive windings included in the plurality of helically formed windings of the coiled reinforcing element.

17. A method of manufacturing an electrode lead adapted for insertion into a human body, the method comprising:
winding an electrode wire in a first winding direction to form a coiled electrode wire;
attaching the electrode wire to an electrode contact;
winding a reinforcing element in a second winding direction to form a coiled reinforcing element;
placing the coiled electrode wire, the electrode contact, and the coiled reinforcing element in an electrode lead mold such that the coiled reinforcing element extends longitudinally together with the coiled electrode wire; and
providing, after placing the coiled electrode wire, the electrode contact, and the coiled reinforcing element in an electrode lead mold, the electrode lead mold with a flexible insulating material such that the coiled electrode wire, the electrode contact, and the reinforcing element are embedded within the flexible insulating material,
wherein:
the electrode lead includes a fantail region that connects to a cochlear implant configured to be implanted within a recipient and that extends to a ground electrode located toward a proximal end of the electrode lead; and
the electrode contact is provided within a distal portion of the electrode lead; and
the coiled reinforcing element:
is only provided within a proximal portion of the electrode lead that does not include the distal portion; and
is only provided in the fantail region that is in the proximal portion of the electrode lead.

18. The method of claim 17, wherein the winding of the reinforcing element in the second winding direction includes winding the reinforcing element around the coiled electrode wire.

19. The method of claim 17, wherein:
the flexible insulating material is silicone; and
the providing of the electrode lead mold with the flexible insulating material includes injecting the silicone into the electrode lead mold such that a flexible body is formed when the silicone solidifies.

* * * * *